United States Patent [19]

Mori

[11] Patent Number: 4,898,438
[45] Date of Patent: Feb. 6, 1990

[54] LIGHT RADIATION DEVICE FOR USE IN MEDICAL TREATMENT

[76] Inventor: Kei Mori, 3-16-3-501, Kaminoge, Setagaya-ku, Tokyo, Japan

[21] Appl. No.: 351,356

[22] Filed: May 12, 1989

[30] Foreign Application Priority Data

Jul. 1, 1988 [JP] Japan ................... 63-164267

[51] Int. Cl.⁴ .................... G02B 6/00; A61B 17/36
[52] U.S. Cl. .................... 350/96.10; 350/96.20; 350/96.22; 350/96.33; 128/362; 128/397; 606/9; 606/16
[58] Field of Search ............ 350/96.10, 96.15, 96.18, 350/96.20, 96.22, 96.23, 96.30, 96.33; 128/303.1, 362, 395, 396

[56] References Cited

U.S. PATENT DOCUMENTS

| | | | |
|---|---|---|---|
| 3,621,181 | 11/1971 | Young | 128/395 X |
| 3,756,688 | 9/1973 | Hudson et al. | 350/96.33 X |
| 3,785,718 | 1/1974 | Gloge | 350/96.33 X |
| 4,576,436 | 3/1986 | Daniel | 350/96.10 |
| 4,625,724 | 12/1986 | Suzuki et al. | 128/303.1 |
| 4,723,825 | 2/1988 | Herold | 350/96.10 |
| 4,785,811 | 11/1988 | Mori | 128/397 |
| 4,794,925 | 1/1989 | Mori | 128/397 |
| 4,796,967 | 1/1989 | Mori | 350/96.10 |
| 4,804,240 | 2/1989 | Mori | 350/96.10 |
| 4,834,484 | 5/1989 | Gorman et al. | 350/96.10 X |

FOREIGN PATENT DOCUMENTS

| | | | |
|---|---|---|---|
| 0208309 | 1/1987 | European Pat. Off. | 128/395 X |
| 2184021 | 6/1987 | United Kingdom | 128/303.1 |

Primary Examiner—William L. Sikes
Assistant Examiner—Brian M. Healy
Attorney, Agent, or Firm—Jordan and Hamburg

[57] ABSTRACT

A light radiation device for use in medical treatment is described. The device comprises a fitted portion for engaging with a light source having a ring-shaped light-radiating end-surface, a cylindrical transparent base portion held in the fitted portion and having one end facing to the light-radiating end-surface of the light source portion and a light-radiating portion comprising of a large number of transparent tapered light-radiating elements arranged at the other end of the cylindrical transparent base portion. The cylindrical base portion is covered with a light-reflecting layer or a clad layer at its outer and inner cylindrical surfaces.

1 Claim, 4 Drawing Sheets

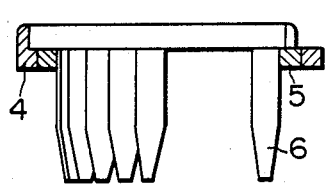
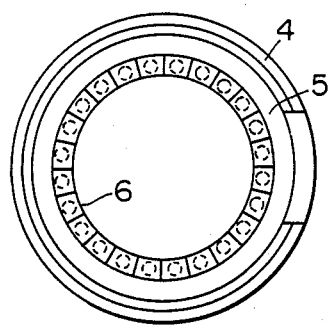
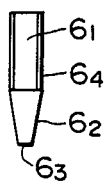
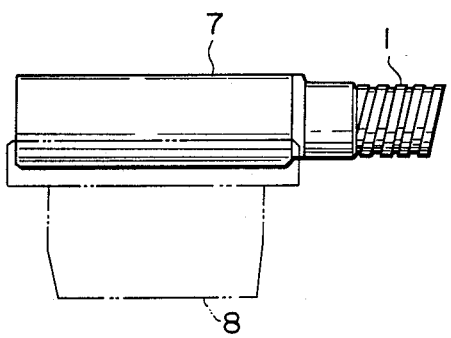

LIGHT RADIATION DEVICE FOR USE IN MEDICAL TREATMENT

BACKGROUND OF THE INVENTION

The present invention relates to a light radiation device for use in medical treatment, in particular, a light radiation device capable of irradiating a patient's scalp with light rays transmitted through a fiber optic cable.

In recent years, a large number of persons suffer from incurable diseases such as gout, neuralgia and rheumatism; or pain from injury scars, bone fracture scars or ill-defined diseases. Furthermore, no one can be free from aging skin which progresses gradually from a comparatively young age. On the other hand, the present applicant has previously proposed focusing solar rays or artificial light rays by using lenses or the like, to guide the focused light rays into a fiber optic cable and to transmit them to any place where the light is needed for illumination or for other purposes as for example to cultivate plants, chlorella, fish or the like. In the process of doing research, it has been found that the visible light not containing ultraviolet and infrared rays is effective not only to promote health and prevent people's skin from aging i.e. by increasing the body's inner activity, but also to noticeably aid in the healing of gout, neuralgia, bedsores, rheumatism, burn scars, skin diseases, bone fracture scars etc. but also in relieving the pain from such diseases.

And further, on the basis of the above-mentioned inventor's discovery, the applicant has previously proposed a light radiating device for radiating visible light rays containing none of the harmful ultraviolet rays and infrared rays with the aim of using it for healing various kinds of diseases, giving beauty treatments and for promoting health.

The present applicant has proposed a light radiation device for use in medical treatment comprised of a fiber optic cable for receiving sunlight or artificial light at its input end, and for transmitting the light therethrough, a hood member installed at the light-emitting end portion of said fiber optic cable and a chair for the patient. The light to be transmitted through said fiber optic cable is one that corresponds to the visible-spectrum light obtainable in the various ways previously proposed by the present applicant. At the time of the medical treatment, a patient is placed in the chair and the visible-spectrum light thus transmitted through the fiber optic cable is radiated onto the diseased part of the patient.

As mentioned above, the light to be radiated onto the diseased part of the patient is the one that corresponds to the visible-spectrum components of the sunlight and free from harmful elements such as ultraviolet and infrared rays. Consequently, it may be possible to make medical treatments safe with no fear of over-exposing a patient to harmful ultraviolet and infrared rays. However, the above-mentioned light radiation device, which is mainly used for healing the above-mentioned various kinds of diseases by radiating the light onto the skin's surface, has proven inadequate in the case of treating a patient's scalp since said light may be obstructed by the person's hair.

SUMMARY OF THE INVENTION

It is an object of the present invention to provide a light radiation device which is free from the above-mentioned drawbacks of the prior art and which is suitable to irradiate the scalp of a patient.

It is another object of the present invention to provide a light radiation device for use in medical treatment, which has a cylindrical base covered with outer and inner light-reflecting layers or clad layers to effectively guide light into a number of tapered teeth at its outlet end for emitting the light and thereby effectively and directly radiating the light rays onto the patient's scalp without being obstructed by hair.

BRIEF DESCRIPTION OF THE DRAWINGS

FIG. 2 is a sectional view for explaining an embodiment of the light radiation device for use in medical treatment according to the present invention;

FIG. 3 is a top view of said device shown in FIG. 2;

FIG. 4 is a fragmentary view for explaining a light-radiating member;

FIG. 5 is a view for explaining an embodiment of the light radiation device when in use;

DESCRIPTION OF THE PREFERRED EMBODIMENTS

Figure 1:
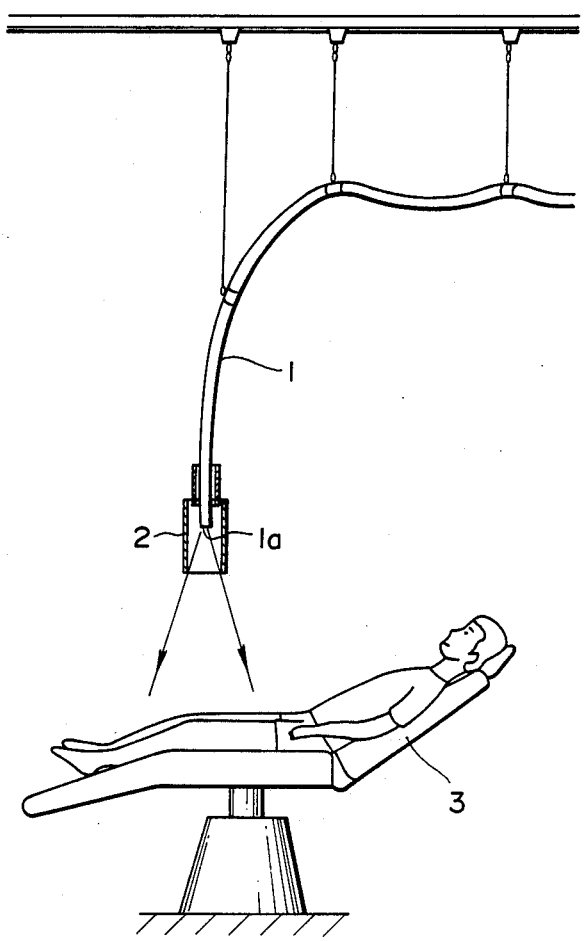
FIG. 1 is a view for explaining an embodiment of the light radiation device previously proposed by the present applicant for use in medical treatment.

FIG. 1 is a construction view for explaining an embodiment of the light radiation device for use in medical treatment as previously proposed by the present applicant. In FIG. 1, numeral 1 designates a fiber optic cable for receiving sunlight or artificial light at its input end, not shown in FIG. 1, and for transmitting the light therethrough. The light to be transmitted through said fiber optic cable 1 is one that corresponds to the visible-spectrum light obtainable in the various ways previously proposed by the present applicant. In FIG. 1, numeral 2 designates a hood member installed at the light-emitting end portion 1a of said fiber optic cable and numeral 3 designates a chair for the patient. At the time of the medical treatment, a patient is placed in the chair 3 and the visible-spectrum light thus transmitted through the fiber optic cable 1 is radiated onto the diseased part of the patient.

As mentioned above, the light to be radiated onto the diseased part of the patient is the one that corresponds to the visible-spectrum components of the sunlight and free from harmful elements such as ultraviolet and infrared rays. Consequently, it may be possible to make medical treatments safe with no fear of over-exposing a patient to harmful ultraviolet and infrared rays. However, the above-mentioned light radiation device, which is mainly used for healing the above-mentioned various kinds of diseases by radiating the light onto the skin's surface, has proven inadequate in the case of treating a patient's scalp since said light may be obstructed by the person's hair.

FIGS. 2 and 3 are respectively a sectional view and a top view of an embodiment of a light radiation device for use in medical treatment according to the present invention. In FIGS. 2 and 3, 4 is a fitting portion, 5 is a ring-shaped holding member and 6 is a light-radiating member held by said holding member in said fitted portion. FIG. 4 is a view of the details of a piece of said light-radiating member. FIG. 4(a) is a top view and FIG. 4(b) is a side view of the light-radiating member 6. In FIG. 4(b), $6_1$ is a base part, $6_2$ is a tapered part, $6_3$ is a rounded light-radiating end and $6_4$ is a light-reflecting layer or a clad layer. The base part $6_1$ and the tapered part $6_2$, which are made of transparent material such as acrylic resin or the like, can be manufactured integrally or can be made separately and bonded to each other integrally with optical paste having the same refractive index as those of parts $6_1$ and $6_2$. A number of light-radiating members 6 shown in FIG. 4 are bonded side by side to each other so as to form a cylindrical light-radiating portion with a light reflecting layer or a clad layer at its outer and inner surfaces as shown in FIG. 3. Consequently, the cylindrical light-radiating portion has a solid cylindrical body formed by parts $6_1$ and a number of light-radiating teeth $6_2$ formed by parts $6_2$ at its one end. Needless to say, it is also possible to integrally form all the light-radiating members 6 and then coat them internally and externally with a light-reflecting layer or a clad layer.

FIG. 5 is a view for explaining an embodiment of the light radiation device. In FIG. 5, 1 is a fiber optic cable for transmitting therethrough the sunlight collected by a solar ray collecting device not shown in FIG. 5, 7 is a sunlight radiation source connected to the fiber optic cable and 8 is the light radiation device for use in medical treatment as shown in FIGS. 2 and 3.

The sunlight radiating source 7 has a ring-shaped light-radiating surface for emitting the light transmitted through the fiber optic cable. When the ring-shaped sunlight radiation source 7 is fitted into the light radiation device 8, that is, the ring-shaped light-emitting surface of the sunlight radiation source 7 is matched with the one end-surface of the cylindrical light-radiating member of the light radiation device 8, the light emitted from the ring-shaped light-emitting surface of the sunlight radiation source 7 propagates through the cylindrical light-radiating member of the light radiation device 8 and then it is emitted through the tapered teeth at the outlet of the light-radiating member. Consequently, when the tapered teeth of the light radiation device are placed on the patient's head, the light delivered through the fiber optic cable 1 can be directly radiated onto the patient's scalp without being obstructed by the hair.

Figure 6:
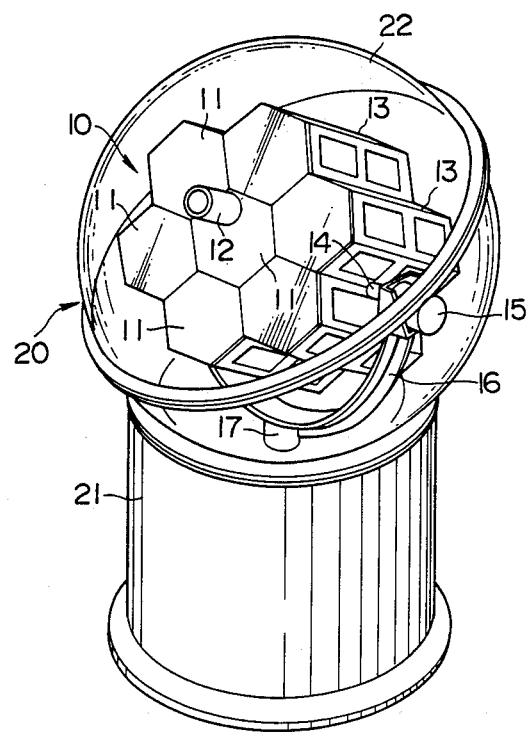
FIG. 6 is a view for explaining an embodiment of a solar ray collecting device to be used for the present invention.

FIG. 6 is an entire perspective view illustrating, by way of example, a solar ray collecting device for guiding the sunlight into the afore-mentioned fiber optic cable 1. In FIG. 6, a capsule 20 for use in the solar ray collecting device is constructed of a cylindrical body 21 and a transparent dome-shaped head 22. As shown in FIG. 6, the solar ray collecting device 10 is accommodated in the capsule when the device is being used. The solar ray collecting device comprises one lens, several lenses or possibly a large number of lenses 11, a solar position sensor 12 for detecting the sun's location, a support frame body 13 for integrally holding the lens 11 and a sensor 12, a first-revolution shaft 14 for rotating the support frame 13, a first-motor 15 for rotating the first revolution shaft 14, a support arm 16 for supporting the lens 11 or the motor 15, a second revolution shaft 17 installed so as to intersect the first revolution shaft 14 perpendicularly thereto, and a second motor, not shown in FIG. 6, for rotating the second revolution shaft 17.

The direction of the sun is detected by means of the solar position sensor 12 and its detection signal controls the first and second motors so as to always direct the lens 11 toward the sun, and the sunlight focused by the lens 11 is guided into the fiber optic cable 1, not shown in FIG. 6, through its end surface set at the focal point of the lens. The guided sunlight is transmitted through the fiber optic cable to wherever the light is needed.

Concerning the above-mentioned solar ray collecting device, several types of devices have been proposed by the present applicant. They are devices respectively having a lens or several lenses (2 to 4 lenses) or a large number of lenses (for instance 7, 19, 36, 61 or 196, 375, 1600 lenses) according to the purpose of its use.

Figure 7:
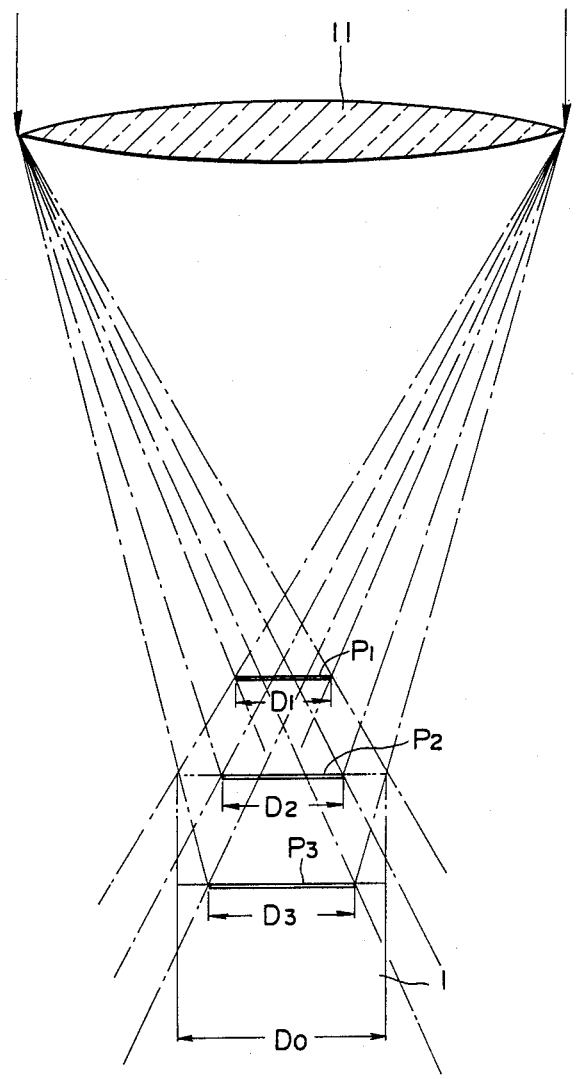
FIG. 7 is a view for explaining an embodiment for guiding the sunlight into a fiber optic cable.

FIG. 7 is a view for explaining how to guide the light rays corresponding to the visible-spectrum components of the sunlight into a fiber optic cable 1. In FIG. 7, 11 is a lens system consisting of a Fresnel lens or the like, and the sunlight focused by the lens system 11 is guided into a fiber optic cable 1 as mentioned before. In the case of focusing the sunlight through the lens system, the solar image has a central portion consisting of almost white light and a circumferential portion containing therein a large amount of the light components having wavelengths corresponding to the focal point of the lens system. Namely, in the case of focusing sunlight through the lens system, the focal point and the size of the solar image will vary in accordance with the component wave-lengths of the light. For instance, the blue color light having a short wave-length makes a solar image of diameter D1 at position P1. Furthermore, the green color light makes a solar image of diameter D2 at position P2 and the red color light makes a solar image of diameter D3 at position P3. Consequently, as shown in FIG. 7, when the light-receiving end-surface of the fiber optic cable 1 is set at position P1, it is possible to collect the sunlight containing plenty of the blue color components at the circumferential portion thereof.

When the light-receiving end-surface of the fiber optic cable 1 is set at position P2, it is possible to collect the sunlight containing plenty of the green color components at the circumferential portion thereof. When the light-receiving end-surface of the fiber optic cable 1 is set at position P3 it is possible to collect the sunlight containing plenty of red color components at the circumferential portion thereof. In each case, the diameter of fiber optic cable can be selected in accordance with the light components to be collected. For instance, the required diameters of the fiber optic cables are D1, D2 and D3, respectively, depending on the colors of the light rays to be stressed, i.e. the blue, green and red colors. In such way, the required amount of the fiber optic cable can be saved and thereby the sunlight containing therein plenty of desired color components can be collected most effectively. And further, as shown in FIG. 7, if the diameter of the light-receiving end-surface of the fiber optic cable is enlarged to D0, it may be possible to collect visible light containing therein all of the needed wavelength components.

The visible light thus obtained is transmitted through the fiber optic cable to the light radiation device according to the present invention, wherein the light is guided into the toothed end portion $6_2$, reflected at the circumference thereof and then emitted from the tips of the teeth $6_3$.

As is apparent from the foregoing description, according to the present invention, it may be possible to provide a light radiation device for use in medical treatment, which has a cylindrical base covered with outer and inner light-reflecting layers or clad layers to effectively guide light into a number of tapered teeth at its outlet end for emitting the light and thereby effectively and directly radiating the light rays onto the patient's scalp without being obstructed by hair.

I claim:

1. A light radiation device for use in medical treatment, comprising a fitted portion for engaging with a light source having a ring-shaped light-radiating end-surface, a cylindrical transparent base portion held in said fitted portion and having one end facing to the light-radiating end-surface of the light source portion and a light-radiating portion comprising of a large number of transparent tapered light-radiating elements arranged at the other end of the cylindrical transparent base portion, characterized in that said cylindrical base portion is covered with a light-reflecting layer or a clad layer at its outer and inner cylindrical surfaces.

* * * * *